United States Patent [19]

Pardikes

[11] Patent Number: 5,730,937
[45] Date of Patent: Mar. 24, 1998

[54] MODULE FOR AUTOMATICALLY CONTROLLING A POLYMER PROCESSING SYSTEM

[76] Inventor: Dennis G. Pardikes, 12811 S. 82nd St., Palos Park, Ill. 60464

[21] Appl. No.: 651,433

[22] Filed: May 22, 1996

Related U.S. Application Data

[63] Continuation of Ser. No. 345,934, Nov. 28, 1994, abandoned, which is a continuation-in-part of Ser. No. 12,412, Feb. 16, 1993, Pat. No. 5,403,552, which is a continuation-in-part of Ser. No. 843,409, Feb. 28, 1992, abandoned, which is a continuation-in-part of Ser. No. 504,910, Apr. 4, 1990, Pat. No. 5,051,940, which is a continuation-in-part of Ser. No. 352,689, May 10, 1989, abandoned, which is a continuation-in-part of Ser. No. 139,075, Dec. 28, 1987, abandoned, which is a continuation-in-part of Ser. No. 871,066, Jun. 5, 1986, abandoned.

[51] Int. Cl.$^6$ ............................................. G01N 21/00
[52] U.S. Cl. ........................ 422/62; 422/111; 436/50; 436/55
[58] Field of Search ........................ 422/134, 62, 111; 436/50, 55

[56] References Cited

U.S. PATENT DOCUMENTS

| | | | |
|---|---|---|---|
| 3,574,553 | 4/1971 | Weitz et al. | 422/62 |
| 4,155,774 | 5/1979 | Randolph | 422/111 |
| 4,263,010 | 4/1981 | Randolph | 436/55 |
| 4,621,063 | 11/1986 | Wyatt et al. | 422/67 |
| 5,230,863 | 7/1993 | Salpeter | 436/53 |

*Primary Examiner*—Lyle A. Alexander
*Attorney, Agent, or Firm*—Laff, Whitesel, Conte & Saret, Ltd.

[57] ABSTRACT

A polymer processing system has a polymer input and an electrolyte input which may be varied independently of each other. The polymer and electrolyte are combined and mixed to provide an out flowing solution which flows through a sensor cell that gives an output signal indicating the concentration of polymer in the solution leaving the processing system. The user repeatedly and incrementally sets the inflows of polymer and electrolyte to provide a preselected variety of concentrations of polymer in the out flowing solution. On each incremental setting, a memory stores information relating the concentration to the output signal. Thereafter, the processing system automatically maintains any desired polymer concentration in joint response to the output signal and the stored information.

22 Claims, 4 Drawing Sheets

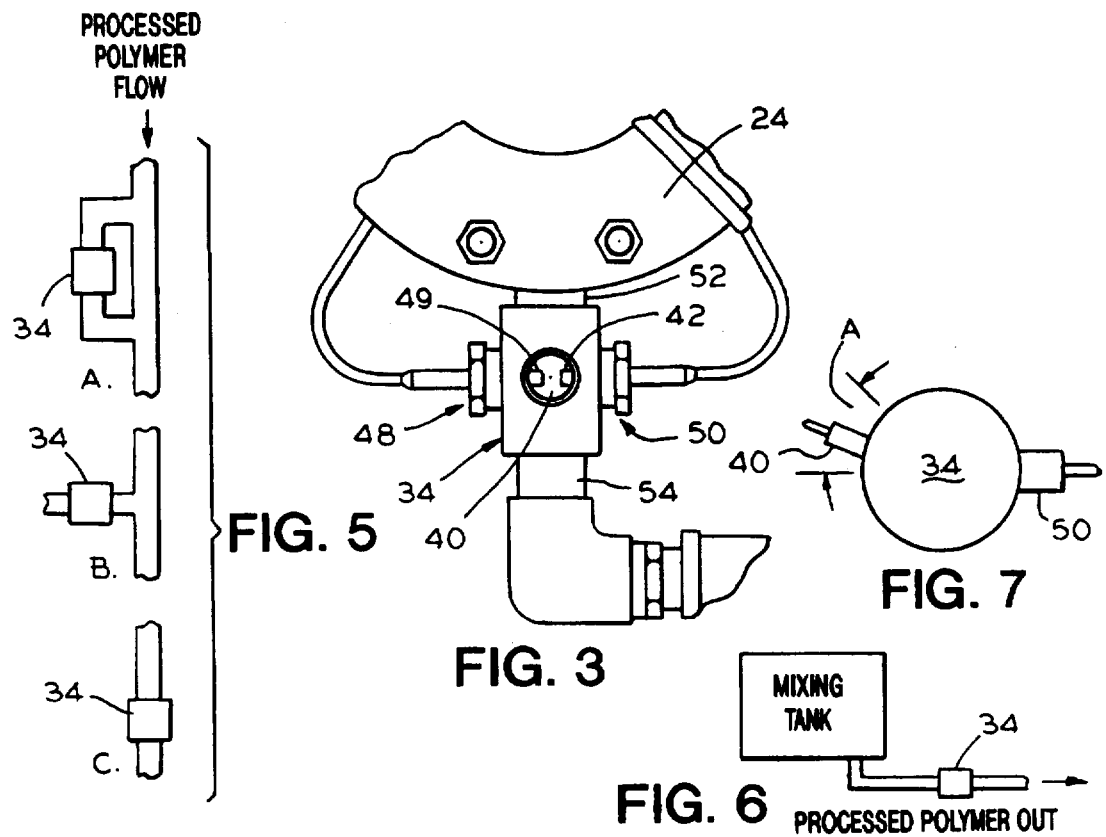
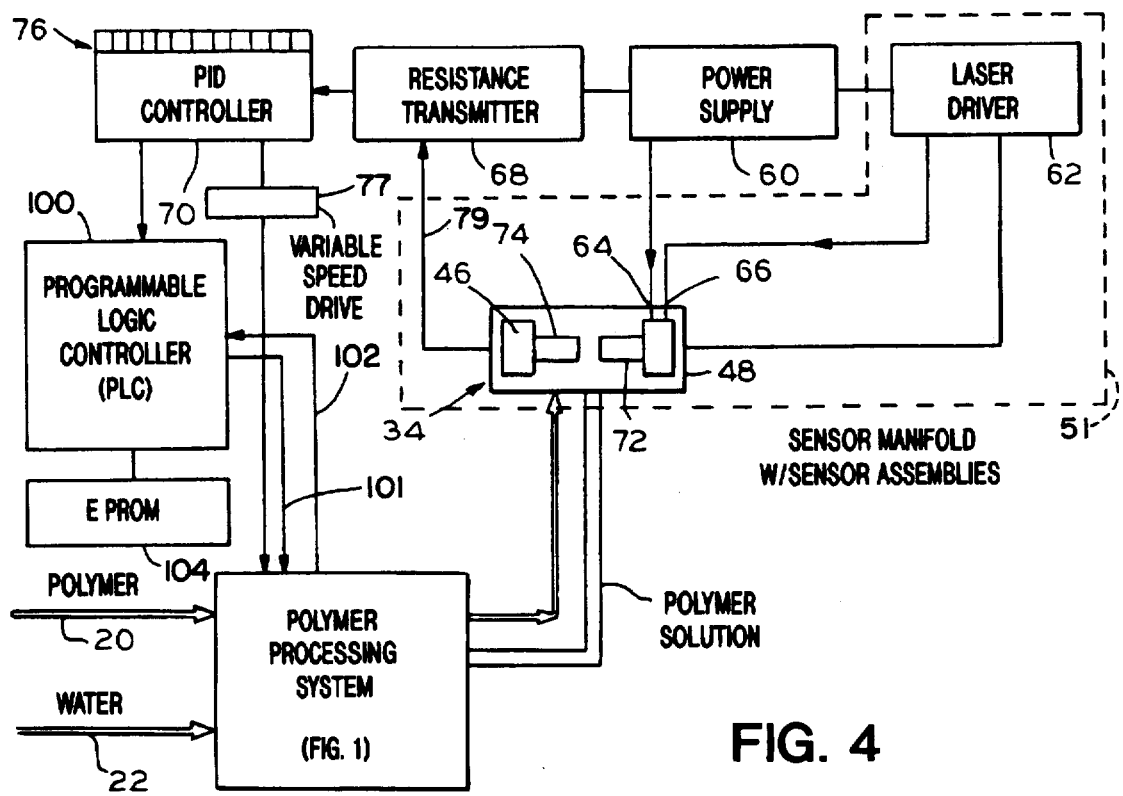

MODULE FOR AUTOMATICALLY CONTROLLING A POLYMER PROCESSING SYSTEM

This application is a continuation of Ser. No. 08/345,934 filed Nov. 28, 1994, now abandoned; which is a continuation in part of Ser. No. 08/012,412 filed Feb. 16, 1993, now U.S. Pat. No. 5,403,552; which is a continuation in part of Ser. No. 07/843,409 filed Feb. 28, 1992, now abandoned; which is a continuation in part of Ser. No. 07/504,910 filed Apr. 4, 1990, now U.S. Pat. No. 5,051,940; which is a continuation in part of Ser. No. 07/352,689 filed May 10, 1989, now abandoned; which is a continuation in part of Ser. No. 07/139,075 filed Dec. 28, 1987, now abandoned; which is a continuation in part of Ser. No. 06/871,066 filed Jun. 5, 1986, now abandoned.

BACKGROUND OF THE INVENTION

This invention relates, in general, to optical analyzers for liquids and liquids containing hydrocarbon and polymer gel constituents, and more particularly to analyzer modules which are capable of automatically monitoring and controlling aqueous polymer compositions with hydrocarbon concentrations of polymer or polymer gel constituents produced through a polymer processing and delivery system.

For convenience of expression, the word "polymer" is used herein to cover all suitable systems without regard as to what they can do or are actually processing. In greater detail, while the inventive analyzer may be used in many fields, to test and analyze many products, it is particularly useful for analyzing polymers. These polymers include—but are not necessarily limited to—synthetically and naturally occurring polymers used in charge neutralization, coagulation, flocculation, and emulsification applications. Another particularly useful application of the invention is in the dairy industry where butter fat is first removed and then back blended into milk. These and similar polymers are blended, activated or otherwise processed in many different system, a few of which are shown in the above-identified patents, patent applications, and similar disclosures.

As a general description, a polymer can be defined as a chemical compound made up of repeating structural units which are comprised mainly of carbon and hydrogen. The structural units, or monomers, are linked together to form long chains in a process called "polymerization". If the monomers are positively charged, the polymer is referred to as "cationic" because it migrates to a cathode. A typical cationic polymer contains positively charged nitrogen ions on some or all of its repeating units. When the polymer is comprised of negatively charged units, it is termed "anionic", again because it migrates to an anode. An anionic polymer, for example, may get its charge from negatively charged oxygen ions. If the net charge on the polymer is zero, it is described as "nonionic". A nonionic polymer can result from either an equal combination of negative and positive units or from an absence of charged groups along its chain.

If a polymer is made up of only one type of repeating unit, or monomer, it is a "homopolymer". If two types of monomer uniformly alternate along a polymer backbone, it is a "copolymer". The number and type of repeating units comprising a polymer molecule determine its molecular weight. Since many monomer units are required to make up a polymer, these weights may be very high, ranging from ten thousand to more than ten million.

"Gels" are colloidal suspensions in which the dispersed, natural or synthetic polymer phase, has combined with the continuous, aqueous, phase to produce a semi-solid material. Gels are also fluid-like colloidal systems having long-chain, nitrogen-containing, macromolecules in a semi-solid form. "Emulsions" are dispersions of high-solids synthetic polymer gels in hydrocarbon oil. All solid synthetic polyelectrolytes result from differences in a processing of a polymer prepared in aqueous solutions, or in an aqueous phase of suspension. The synthesis results in a rigid, tough, rubbery gel. Processing the tacky gel particles, with heat, produces the "dry" or "powder" solid polyelectrolyte product.

In general, an activation of liquid polymers is a compound/complex continuum of multistage organic chemical reactions. Depending on the characteristic of the polymer, the activation may require one or more distinctive and successive stages.

Liquid emulsion polymer or micro emulsion polymer (whether 25% to 40% active inverse-emulsions, or 50% to 70% active dispersions) require two distinct processing steps to completely activate the aqueous polymer solution product. These two steps are inversion and aging, similar to the systems described in the above-identified patent applications. In the inversion phase, polymer processing systems "break" the emulsion by subjecting the mixture of high-active-solids polymer gel particles to high-energy, high shear, pressure and mixing gradient forces which instantaneously disperse the continuous oil phase and release the discontinuous polymer gel particles, thereby freeing the polymer to dissolve in the dilution water through hydration and molecular diffusion. In the aging step, the liberated polymer particles are allowed to hydrate and diffuse, in-line or in specially designed holding tanks.

Solution polymers (whether 2% to 7% high molecular weight active or 5% to 60% low molecular weight active) may require only one processing step. The high turbulence high energy blending associated with the above-mentioned systems are usually enough to provide an active in-line homogenous aqueous polymer solution.

The ideal polymer processing system should perform at least two functions. (1) It should provide an active and homogenous polymer solution and; (2) should maintain a desirable relationship (ratio) between the volume of solvent or diluent (water) and the volume of polymer (solute). Additionally this relationship or ratio should be adjustable over a usable range. The polymer particles and associated constituents in a ratio with the aqueous diluent, form a polymer composition which is the "concentration" of the solution.

The concentration of the polymer solution is an important aspect. Too great a concentration causes a polymer overdose result with a negative effect. Too small a concentration causes a polymer underdose that has a similar negative effect. Therefore, it is extremely important to maintain the proper dosage range when applying a polymer. Controlling the concentration of the polymer is one important variable.

Another aspect of maintaining proper polymer concentration involves the "breaking" or inversion of an emulsion type polymer. Too great a dilution results in a low concentration which might wash away necessary inverting agents called "activators" or "surfactants" which are useful in emulsifying hydrocarbon carriers. At the start of the polymer processing procedure, the concentration of a polymer solution is established by setting the diluent flow rate and the polymer flow rate at a desired ratio. For example, a 1% solution concentration set point is established by rationing 1 part of polymer to 100 parts of diluent. (Polymer to Water 1:100)

An ideal analyzer should continuously sense the polymer particles and associated constituents freed in the aqueous medium and should provide pertinent concentration information. If the sensed concentration begins to depart from the desired setpoint, signals from the analyzer should be fed back to adjust the polymer processing system. While the system is being so adjusted, the analyzer should monitor to avoid over correction. When the polymer mixture approaches the desired concentration setpoint, the process should be stabilized and then maintained there.

Other fluids, liquids, gels and the like have similar problems which may be addressed by the invention. For example, milk and milk products may also be monitored continuously by the invention. Thus, for example, during processing, milk is first separated from its butter fat and then the butter fat is blended back into the milk at the appropriate concentrations. This process may be monitored or controlled by the invention.

In the inventive system, a sensor manifold assembly or sample block or sample chamber (hereinafter "sample chamber") may be either a stand alone component or a part of another assembly, such as a premix manifold. The sample chamber can be installed to accept either a full process flow or a partial process or a bypass flow. These alternatives give great flexibility as, for example, when adding the inventive module for automatically controlling polymer processing to an existing system while retrofitting an installation.

In one instance the sample chamber may be placed downstream of the polymer processing system at a cascaded location after the primary solution has been blended or inverted, etc. and where there may be further dilution by way of secondary or tertiary dilutions. Also, by way of another example, the module for automatically controlling the polymer processing system can be used in the well known cascade control fashion by monitoring the polymer solution as it exits a holding vessel or aging tank in order to provide a consistence of polymer concentration which heretofore has been unheard of. This is particularly useful in processes like paper making where the polymer is critical to the wet end chemistry of the paper machines.

In the structure set forth in U.S. patent application Ser. No. 08/012,412, filed Feb. 16, 1993, the system was operated with a set point. For example, in order to provide the 1% solution concentration described above, the input of polymer is set at some value in terms of gallons per minute. Then, the input of diluent electrolyte is set at 100 times that value, again in terms of gallons per minute. Hence, the output solution will be 1 part polymer and 100 parts diluent.

When the system reaches equilibrium, a suitable command is given. Thereafter, the system automatically operates at a 1% solution concentration which existed when the command was given. If the user wishes to operate the system at, say 0.5 parts polymer and 100 parts diluent, the set point procedure is repeated. Thereafter, the system operates at a ratio of 0.5 polymer per 100 parts diluent. However, now the system can no longer operate at the ratio of 1 part polymer, per 100 parts diluent unless the reset procedure is followed. This means that the system Ser. No. 08/012,412 is always dedicated to operate at some fixed ratio. It can not operate at any other ratio unless the preset procedure is repeated.

This problem occurs because polymers do not have linear response functions. In fact, each polymer has its own characteristic profile curve. Few of the polymers share the same characteristic curve. Therefore, unless there is a very unusual situation, the users of the inventive system almost always have to refer to a different unique characteristic curve each time that a new polymer is processed.

Accordingly, an object of the invention is to provide new and novel concentration analyzers which do not require resetting in order to process many different concentrations of a polymer in a liquid. Here, an object is to provide a continuous sensing of the concentration of a polymer or other liquid, semi-liquid, gel or the like and to relate that concentration to a non-linear relationship. In this connection, an object is to provide for operating a polymer processing system with anyone of many solution concentrations which are automatically maintained without requiring the calibration of a new set point each time that the ratio of polymer to electrolyte is changed.

Another object of the invention is to provide a production system which may be monitored and automatically adjusted, continuously.

In keeping with an aspect of the invention, these and other objects are accomplished by first "profiling" a characteristic curve or table of information into a computer memory in order to describe a particular polymer. In greater detail, a light source emits a controlled amplitude and frequency of coherent light (laser) energy which is scattered and absorbed by the polymer material dispersed throughout an instantaneous aqueous sample of a monitored material flowing continuously through a sample chamber. The source of light energy is located at an adjustable distance from one side of the sample chamber. An optical receiver (a photoresistor with a selectable filter) measures the amount of light received on the other side of the sample chamber and generates an output signal which may be converted into a usable process control signal.

In order to profile the curve, the operator repeatedly sets the inflows of polymer and an electrolyte, such as water, and then, after each such setting, stores a memory of the relationship between the set inflows and the process control signal, thereby producing a curve or a table of information for the particular polymer being processed. A process controller (microprocessor or microcomputer) compares the usable process signal generated responsive to the received light to the stored characteristic curve in order to detect any deviation of the actual concentration or ratio of polymer to electrolyte to the theoretical ratio described by the characteristic curve or table of information.

The process controller display can be configured to read in any suitable terms, such as percent concentration, active polymer solids or any other relevant engineering unit or scale.

When the monitored system has feedback, the receiver output may be applied through a feedback control loop so that the process controller may be programmed to proportionally monitor and adjust a processing system such as a polyelectrolyte concentration by automatically controlling the polymer processing and delivery system itself.

BRIEF DESCRIPTION OF THE DRAWINGS

A preferred embodiment of the invention is shown in the attached drawing, wherein:

FIG. 3 pictorially shows how the inventive sensor and sample chamber is connected into a polymer processing system, such as that shown in FIG. 1;

FIG. 4 is a block diagram of the inventive system;

FIG. 5 schematically shows alternative ways of connecting the inventive module into a polymer flow system;

FIG. 6 schematically shows a cascade coupling of the inventive module;

FIG. 7 graphically illustrates how the angular displacement between a laser light source and a detector may be varied;

DETAILED DESCRIPTION OF THE INVENTION

Figure 1:
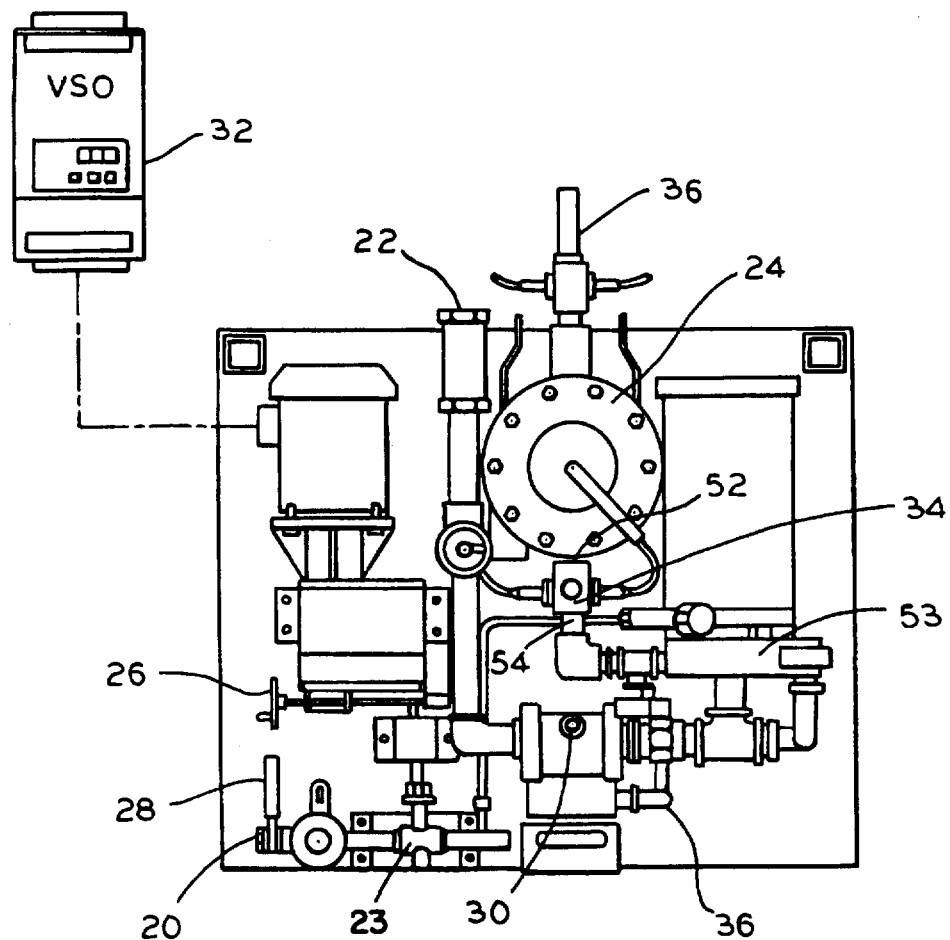
FIG. 1 is a pictorial representation of the mechanical aspects of a system incorporating the invention.

Broadly, a polymer processing system (FIG. 1) has polymer and any suitable electrolyte (hereinafter called "water" for convenience of expression) which are introduced via intake ports 20, 22, respectively. A polymer pump is shown at 23. If one part of polymer is introduced via port 20 while one hundred parts of water are introduced via port 22, the concentration is 1% polymer. The polymer and water are mixed in any suitable and known way and then fed through a mixing pressure regulator 24. Various mechanical control handles 26, 28, 30 may be manually adjusted as may be required. These adjustments may be purely mechanical (as opening or closing valves); or, they may be settings of adjustments on electrical controls/actuators.

On control panel 32, various electrical switches or the like may be used to program the system. As here shown, by way of example only, the panel provides a variable speed control. Almost any kind of adjustable device may be accommodated. The inventive sensor sample chamber 34 is here shown, by way of example at the inlet port of the mixing pressure regulator 24 to continuously monitor the solids content of the fluid flowing to the mixing pressure regulator 24. Alternative locations 36, 36 might place the inventive controller/sensor at the output of the system while another location might be on the recycle leg of the polymer mixing loop. The controller/sensor may also be located at any other suitable location in the system.

FIG. 4 shows a block diagram of the electronic controls for the inventive system. The electronic modules depicted in FIG. 4 are located in the main control panel 32 of the system described in FIG. 1. Most of the polymer processing system of FIG. 1 is generally shown in the lower left-hand corner of FIG. 4.

Three elements form the essence of the automatic polymer solution controller system:

a sample chamber, sensor manifold assembly or sample block;

an electronic module; and a process controller.

The sample chamber or sensor manifold assembly 34 (FIG. 2) has a flow chamber 40, in a housing with a transparent viewing port 42, a selective light filter 44, a cadmium sulfide (CdS) photoresistor 46, and a coherent light source (semiconductor laser) emitter 49. The assembly of FIG. 2 has threaded ports which accept diode assembly 48, and resistor lens detector assembly 50.

Figure 2:
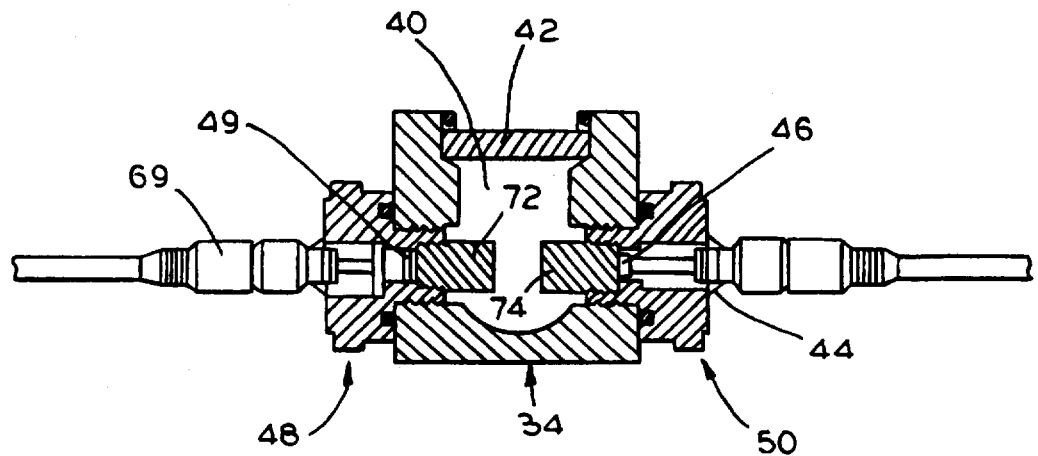
FIG. 2 is a cross sectional view of the inventive sensor in connection with a sample chamber.

FIG. 4 shows the assembly of FIG. 2 built in a modular design which incorporates the components of FIG. 2 and a laser drive means 62 built into a single housing 51 which offers a more compact size and reduces the chances for a diode failure. This module 51 is a commercial product (Model VLM 2-5C) sold by Applied Laser Systems, 2160 N.W. Vine Street, Grants Pass, Oreg. 97526.

The laser diode assembly 48 incorporates a semiconductor diode 49, heat sink, lens, static shielding and pin connector housed in a cylindrical threaded body designed for ease of removal from the sample cell. One exemplary laser diode 49 produces light which has a visible light wave length of $\lambda=670$ nm. Depending on the type of laser used, wavelengths can vary from approximately 300 nm through infrared (>700 nm). In one example, a laser diode with a wavelength of 780 nm may be used in conjunction with a photodiode detector (i.e., a silicon photocell) to take full advantage of polymer compositions that respond favorably to the infrared spectrum. In another example, an ion laser operating at 514 nm may be used for polymer compositions which respond favorably to this wavelength. For both examples, the appropriate lasers would be fitted for use in the module for automatically controlling the polymer system.

The laser light is by far the most efficient way of reading through the polymer solution. However, at the margin of utility and for some polymer solutions, white light may be used instead of the laser light. Therefore, for the convenience of expression, the term "coherent" light is to be construed as any light suitable for a particular polymer solution.

The sample chamber (FIG. 2) may be installed to use either a bypass (FIG. 5A), a partial flow (FIG. 5B) or a full and unrestricted solution flow (FIG. 5C), depending on its relative location in and the nature of the polymer processing system (FIG. 1). FIG. 6 shows the inventive module at a cascaded location downstream of a mixing tank. The output in any of the connections of FIG. 5 or 6 may be either part of a feedback loop or the output of the system. The flow of a polymer solution through sample chamber 34 (FIG. 2) has to be fast enough to respond to process changes and slow enough so as not to cause an undue turbulence and thus to prevent an efficacious reading.

FIG. 3 shows one example of a connection of the sample chamber assembly into the polymer processing system. In greater detail, a pipe 54 leads from a polymer mixing chamber 53 (FIG. 1) into the sample chamber housing 34 and pipe 52 leads from the housing 34 to the pressure regulator 24 so that the polymer solution flows through the sensor chamber housing 34 during normal processing. The inside diameter of the flow chamber 34 can range from 0.302" to more than 12.0" and flows can range from 0.25 gpm to 5000 gpm. Typically, a sample cell will be designed for a flow velocity of 1 to 10/ft sec. However, a range of 0.3 to 25.0 ft/sec, or more, is possible depending on the rheology of the fluids.

During the flow, a light from laser source 49 (FIG. 2) shines coherent light through the solution in chamber 40 toward the receiver assembly 50. The characteristics of the solution flowing through housing 34 are detected by the differences in the readings taken at the receiver assembly 50.

The sample chamber 34 is designed for a direct opposing scan of the light emitter and detector which seems to be the most efficient arrangement for most polymer solutions. However, there are cases where an off axis scanning is preferred. Basically, the light emitter diode 49 and detector 46 may be set at any suitable angle with respect to each other. This setting tends to emphasize a certain type of particle reflection which is not typically enhanced in direct opposition scanning. The angle of particle reflection A (FIG. 7) may be in the range from 0° to 60°; however, sometimes greater angles may be used if testing warrants it.

In many cases, the level of partial hydration of certain polymers with respect to efficiencies of invention and on blending, aging, etc., may lend itself to angles greater than 60°. Where this is the case, the lenses can be set at 70°, 90°, 120°, 180° or any angle in between. In this arrangement, the optical output of the emitter cell could be adjusted to compensate for the more radical off axis lens angles.

The automatic polymer solution controller electronic module (FIG. 4) integrates several functions into a single unit. The first function of the module is to provide an adjustable power supply 60 to power a semiconductor laser diode driver 62 and resistance transmitter 68. A special feature is included to protect the semiconductor laser in that power from the power supply 60 is routed to an external connection 64 on the sensor housing 34. A lead from another external connection 66 is connected to the laser driver 62.

In this inventive example, the semiconductor laser diode 49 (FIG. 2) is powered by a laser driver circuit 62 rated to deliver up to 150 mA of power. An on board potentiometer enables this driver to be adjusted to the desired output power. The driver can either provide a constant light or optical output via a pin diode feedback or provide a constant current source for the laser diode. This is a selectable feature. The optical feedback loop is designed to maintain a constant light output which is independent of temperature variations at the diode. The feedback loop remedies this temperature caused problem by compensating the amount of drive current delivered to the diode so that the driver current is automatically adjusted to maintain the same light output level.

Through the use of a plug 69 (FIG. 2) on the diode lens assembly, the connection is made to diode 49 before the diode drive board connection is made. This important feature protects the diode 49 from destructive voltage spikes if the diode connector should be removed while it is receiving power. Additionally, the power supply lead pins on the printed circuit board holding the module of FIG. 4 are mechanically shortened to prevent supply problems caused by spikes if the module is removed or replaced while the processing unit is powered.

The delivery of power to the diode automatically shuts down within milliseconds after the detection of a destructive voltage spike. This feature is built into a laser driver circuit. This is particularly useful when attempting to disconnect or reconnect a diode with the power on. This circuit enhancement both prevents the diode from failing due to a sudden spike, and eliminates the need for special connectors designed to prevent this. This circuit also prevents a user from removing the light emitting diode from the sample chamber while the laser is operating. This is also an important consideration in meeting certain classes of regulating compliance codes.

The module for automatically controlling the polymer solution also includes a resistance transmitter signal conditioning device 68 (FIG. 4) which has separate zero and span settings. The resistance transmitter 68 accepts a resistance signal from the receiving sensor 46 and converts it into a proportional analog output. In effect, resistance transmitter 68 is a translator for converting the "language" of sensor 46 into the "language" of PID (proportional integral derivative) controller 70. The PID controller 70 is a standard commercial electronic product, such as those sold by Yokagawa (Model UT 40) and by Powers, Model 535.

Because semiconductor lasers are sensitive to heat from many sources, one has to be particularly careful when monitoring processes that are carried out at a temperature which is higher than ambient temperatures. When running a high temperature solution (above 50° C.) through the sample chamber 34, remoting the emitter and detector cells prevents conductive heat damage to the diode. In the inventive system, fiber optic cables may be fitted to adapter lens housings at the sample chamber and then routed into another enclosure (i.e., control panel) where the emitter and detector are placed away from the heat source. The fiber optic cables are then terminated at ends of the emitter and detector assemblies.

The losses experienced through fiber optic transmission inefficiencies are compensated by increasing the optical output of the laser. Most laser diodes are operated at or above their threshold current values. This is often 70% to 90% of their maximum current value. Thus, for a diode with a maximum operating current value of 100 mA, the threshold current might reasonably reside somewhere around 80 mA. The threshold current is defined as the point in the radiant power output curve where the diode exhibits the special laser light qualities. For most applications, this is where the inventive system seeks to operate.

The electronic PID controller receives the output from the resistance transmitter 68 and displays it at 76 as a process value. The output from the PID controller is then used to control the speed (in this example) of a neat polymer injection pump 23 (FIG. 1) via variable speed drive 77. Hence, there is a feedback control loop from PID controller 70 to the polymer processing system (FIG. 1), sample chamber 34, resistance transmitter 68, and back to controller 70, which continuously adjusts the polymer processing system.

In operation, the polymer solution passes continuously through the housing of the sensor chamber 36 (FIG. 2). The laser light source 49, operating in this example at a wavelength of 670 nm, is positioned inside the housing of sensor chamber 34 and behind a suitable lens assembly 72 located on one side of the monitored solution stream. The light passes from the laser source through the lens 72 and then through the polymer solution. After passing through the polymer solution, it enters a second lens assembly 74 on the opposite side of the solution stream. Located inside and behind the second lens assembly is a light selective filter (approximately 670 nm) and a CdS photoresistor 46.

The frequency which is selected for the laser depends on the type of polymer that is being monitored. Most synthetic polyelectrolytes, such as dispersions, emulsions, and natural polymers (corn starches, for example) respond well at the 670 nm wavelength. Solution polymers work best at or near infra-red wavelengths. However, for the entire range from visible light through infrared, all frequencies can be used to take advantage of unique molecular footprints and equivalent weights.

The light intensity which is received at the resistor lens assembly 74 (FIG. 2) passes through a light selective filter prior to entering the CdS cell 46. By matching the light selective filter with the laser frequency, ambient light entering the sample chamber 34 through the viewing window 42 does not have a disruptive effect on the reading from CdS cell 46. Any small percent of the ambient light that has wavelengths that pass through the light selective filter are considered background noise which may be calibrated out of the reading, under almost all conditions.

The intensity of the light which is received at the resistor lens assembly 74 varies with the concentration of the polymer solution.

The resistance of the CdS cell 46 is variable with the intensity of the light. Due to these two relationships acting in conjunction with each other, the output resistance becomes directly proportional to the concentration of the polymer solution.

The resistance of the CdS cell 46 is measured and converted into a process control signal by resistance transmitter 68 and PID controller 70. This signal may become a manually selected setpoint which is entered into the PID or the programmable logic controller ("PLC") 100, which is a standard commercial item (FANUC Series 90-30) manufactured and sold by the General Electric Company. The PID controller 70 output signal is a control signal for adjusting the processing system of FIG. 1.

Since it has been assumed for descriptive purposes that the controlled device 32 (FIG. 1) is a variable speed drive in FIG. 1, the usable output signal varies the speed of a positive displacement polymer injection pump 23. As the concentration of the polymer solution tends to decrease (i.e., water flow increases), neat polymer solids decrease, etc., the PID controller 70 (FIG. 4) increases its output signal, thus increasing the speed of a positive displacement pump 23. This causes more polymer to be metered to the polymer processing unit, thus increasing the concentration of the polymer solution. The usable output signal may cause the percent of polymer concentrate and active polymer solids to be displayed at 76.

Another example would incorporate the use of a water flow control valve at a location where the polymer injection pump stays constant and the water flow is adjusted for concentration control.

The system of FIG. 4 includes the programmable logic controller ("PLC") 100 which is connected to the polymer processing system of FIG. 1 in order to send at 101 and receive at 102 information relating primarily to flow rates of polymer at inlet 20 and water at inlet 22, expressed in terms of gallons per minute, or the equivalent. The laser sensor 34 sends its reading to the PLC via the resistance transmitter 68 and PID controller 76. The PLC stores information which it receives or generates in an EPROM 104.

Figure 8:
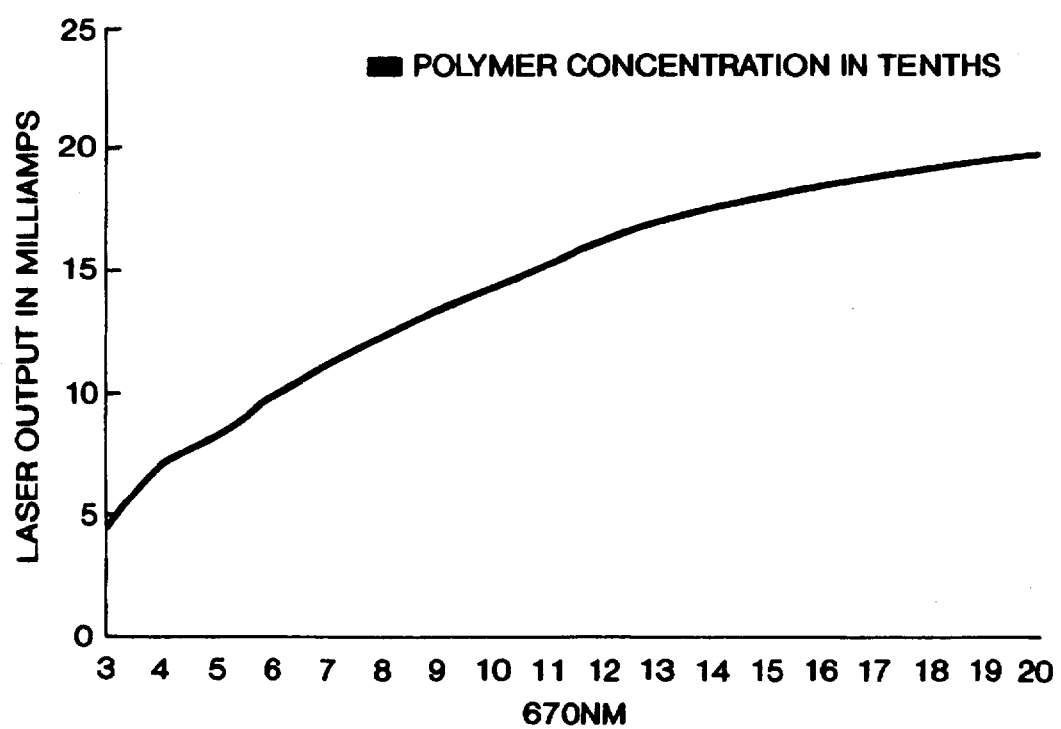
FIG. 8 is an exemplary graph showing a hypothetical non-linear relationship between the laser signal output and polymer concentration.

FIG. 8 is a graph which shows a characteristic curve for an exemplary and hypothetical polymer. The same information could be stored in a look-up table. Each polymer has its own individual curve which should be used when that particular polymer is being processed. This information could be stored in many different ways.

On the other hand, one desirable characteristic of the invention is that it is adapted to be controlled by a person such as computer terminal operator, or the like, who is skilled at working on a computer terminal; however, it is, perhaps unlikely that the operator will know very much about characteristic curves of a polymer. Therefore, an object of the invention is to enable the terminal operator to enter a curve or table of information, such as in FIG. 8, without being familiar with the polymer.

In greater detail, the curve of FIG. 8 is "profiled" into the computer. In this case, custom "profiling" is a technique for entering information responsive to the use of an internal computer construction without requiring the operator to know the specifics of the information that is being entered. That is, the information is entered as if it were being "profiled" by the computer itself.

FIG. 8 has the laser produced output readings (i.e. the milliamp reading on wire 79, FIG. 4) on the vertical scale and the polymer concentration (read in tenths of a percent) on the horizontal scale. Therefore, the vertical scale is 0–25 milliamps and the horizontal scale is from 0.3% to 2% concentration of polymers in the output solution.

In order to profile or paint the curve into the computer, the operator first adjusts, in incremental steps, the polymer inflow at inlet port 20 to have an inflow rate of 0.3 GPM (gallons per minute) and the water inflow at inlet port 22 has 100 GPM. As soon as the two inflows are mixed and equilibrium occurs, the PLC 100 computer or alternatively the PID stores a memory of the ratio of inflow rates and the laser output in an EPROM 104. This ratio is the first recorded point on the curve of FIG. 8, representing the first incremental adjustment of the inflows to 0.3% polymer concentration in the output solution. Then, the operator resets the inflows at inlet ports 20 and 22 in the next incremental step and the PLC stores a memory of the next point on the curve of FIG. 8 in the EPROM 104, representing the second incremental adjustment of the inflows, i.e. the milliamp reading at 0.4% polymer concentration in the output solution.

The process is repeated in incremental steps which may be as fine or as coarse, per step, of the adjustments as the operator may wish to make.

Depending upon the nature of the user needs, the memory stored in EPROM 104 may be any suitable number of points to generate a curve that is profiled into memory. Also, depending upon user needs, one or more curves may be stored at addresses so that, in the future, the operator only has to enter an address code to recall any curve that has been stored in the past. This way, it is only necessary to enter a code which identified the polymer that is being processed.

Or, the EPROM 104 may be adapted to store a single curve which is erased and replaced each time that a new polymer is introduced into the system of FIG. 1. If a user does not change the polymer being processed very often, this record, erase, and re-record may be the most economical.

Once the curve of FIG. 8 is profiled into the memory at EPROM 104, the PLC 100 or alternatively the PID generates and sends process control signals at 101 which controls and adjusts the inflows of polymer and electrolyte at the two input ports at 20 and 22. This control holds a selected level of polymer concentration in the solution delivered at the outflow port, as read by the laser sensor of FIG. 3. For example, if a polymer concentration of 1% is desired in the out flowing solution, the computer terminal may be adapted so that operator only has to push "1". For, say, a 0.75 concentration, the operator pushes "0.75". Of course, any suitable arrangement including words (such as "skim milk", "lo fat", "whole milk", etc.) may also be provided for an operator to punch when a process begins.

For better performance, there are instances where the module for automatically controlling the polymer system can be tuned to operate below the threshold value of the laser. This is particularly true for polymer solutions with lower densities. In this case, the laser acts as a light emitting diode of a monochromatic nature with marginal coherency at a much lower energy level. In the inventive system, the laser driver can be adjusted to operate below the threshold current in order to accommodate such an application. This is useful when applying the unit to a broad range of applications. The flexibility inherent in this feature provides a means for processing different solutions of different concentrations, within the capability of the module for automatically controlling a polymer system.

One such application involves the use of the module for automatically controlling a system in the dairy industry. The module can be used as a standard component for evaluating the butter fat content in milk where the dairy industry typically back blends butter fat into milk. The module enables dairies to measure and adjust the milk/butter fat ratios to determine whether the milk is skim; <1%, low fat; 1-2%, whole 3-4%, etc. When used in a feedback loop, the module interfaces with a dairy central process computer in order to control and adjust butter fat content on a continuous production basis.

Figure 9:
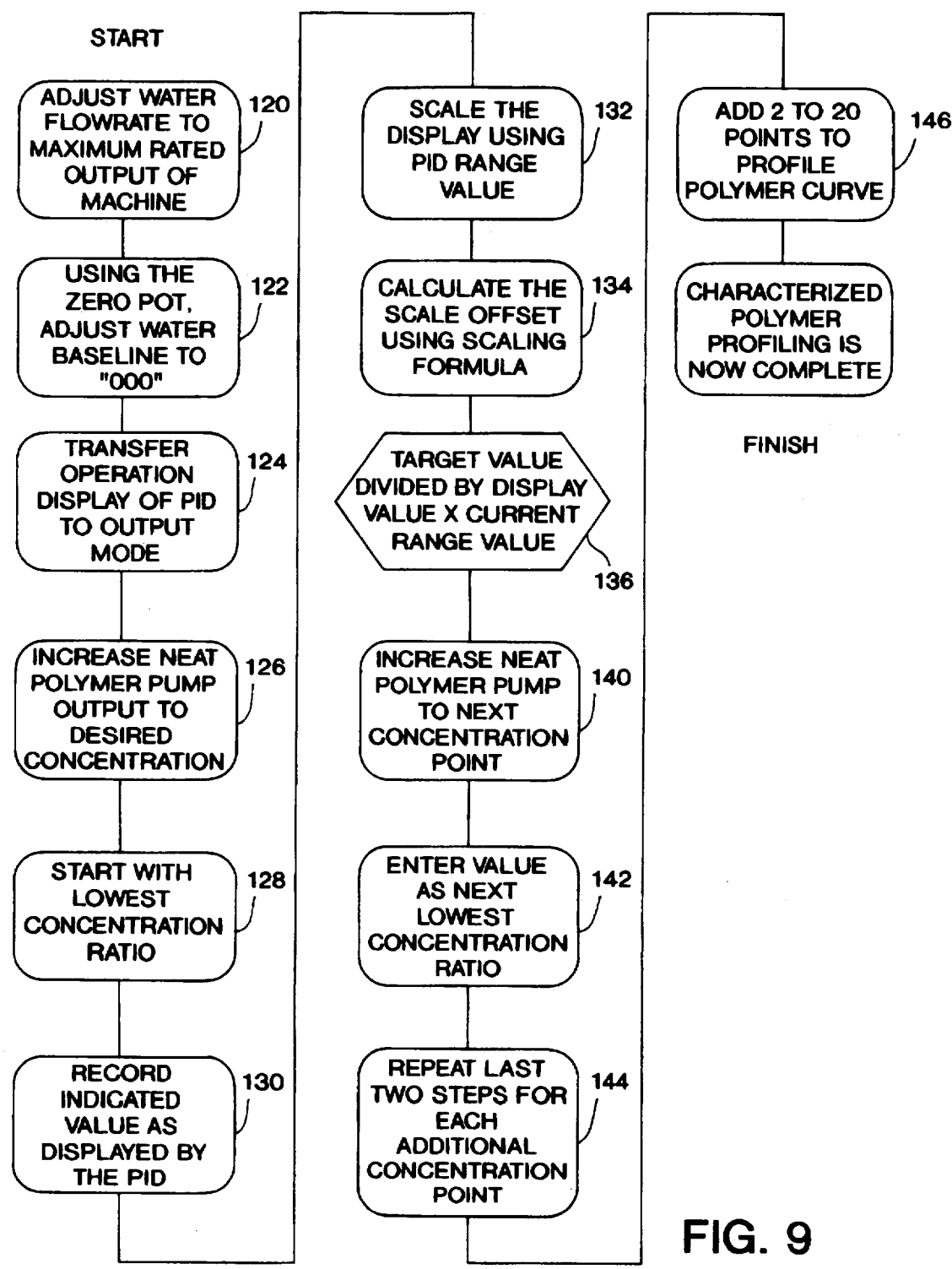
FIG. 9 is a flow chart showing the operation of the inventive programmable controller.

The procedure for profiling a polymer processing curve is shown by the flow chart in FIG. 9, which is written in terms of a manual procedure. However, it should be understood that much of the procedure may be performed by a microprocessor operating under human supervision.

First, the inventive polymer processing system is switched on and brought up to speed. Then, the electrolyte or water flow rate is adjusted at 120 to a maximum volume for the system. A digital readout on the machine is then adjusted at 122 to give a base line reading of "000" at the maximum water flow.

The display 76 of PID 70 (FIG. 4) is transferred at 124 to an output mode which will allow the user to manually adjust the speed of pump 23.

The neat polymer pump is adjusted at 126 until the desired concentration is reached. For the first point or lowest concentrated ratio on the curve of FIG. 8, the first concentration of polymer will be set (128). For example, in the case of the graph of FIG. 8, the first setting is at 0.3% polymer (99.7% water).

The value being displayed at 76 on PID controller 70 is recorded at 130 while the system is operating at the set concentration (0.3% in this example) of the first setting which was made at step 128. This recorded value may be adjusted at 132 to reflect any suitable scale that is being used. If the graph is such that the point 0.3% is offset from either the vertical or the horizontal axes by some distance, a calculation to provide such offset is made at 134.

The user may or may not be satisfied by any given reading. As with all laboratory test readings, it may be desirable to take repeated readings and then average out the errors. Also, there are rounding errors, which might leave the user with an unacceptable level of possible errors. Stated another way, a redundancy of reading brings greater reliability.

Therefore, at 136, the program of the FIG. 9 flow chart provides for a reiteration of the program calculation results. On each iteration, reliability is increased by, in effect, dividing a calculation error in half. The repeated computations are made to divide a desired target value by the current PID display 76 and then multiply the resulting value by a range value, thereby reducing the error by one-half on each iteration.

At 140, the polymer pump is adjusted to the next higher level of polymer concentration. Assuming that the user wishes to profile every point on the graph of FIG. 8, the user next sets the concentration of the outflowing solution to 0.4% polymer. The steps 130–136 are repeated at 142.

In like manner, as shown at 144, steps 140, 142 are repeated for each resetting of the polymer concentration shown in FIG. 8 which is to be recorded.

As shown at 146, the system is designed to record any desired number of points from 2 to 20 on the curve of FIG. 8. The computer will draw the best and smoothest curve through the recorded points, as shown in FIG. 8.

Those who are skilled in the art will readily perceive how to modify the invention. Therefore, the appended claims are to be construed to cover all equivalent structures which fall within the true scope and spirit of the invention.

The invention claimed is:

1. An automatic controller in combination with a polymer processing and delivery system for continuously controlling production of a polymer solution during operation of said polymer processing and delivery system, said controller comprising optical analyzer means using coherent light for continuously monitoring a concentration of polymer solids and controlling a polymer solids/hydrocarbon concentration of a polymer solution product at least while the system is in operation, said analyzer means including a sample chamber coupled to continuously receive and at all times contain an instantaneous aqueous sample of said polymer solution product, means for emitting said coherent light with a controlled amplitude and frequency into said sample, said light energy being scattered and absorbed by the polymer material dispersed throughout the instantaneous aqueous sample within the sample chamber, optical receiver means for measuring an amount of said coherent light energy received after said light passes through said instantaneous sample, means for converting an output from said receiver means into a usable process control signal for controlling said polymer system in order to maintain a desired concentration and viscosity in said liquid, wherein said automatic controller controls a concentration of any selected one of a plurality of different types of polymers in an out flowing solution of said polymer processing and delivery system, said system including means for feeding an adjusted inflow of a selected polymer into said processing system, said selected polymer being one of said plurality of types of polymer, means for feeding an adjusted electrolyte inflow into said system, means for delivering an outflow from said system comprising a solution having a combination of said selected polymer and electrolyte with a concentration of said selected polymer fixed by a relative proportion of said inflow of said selected polymer to said inflow of electrolyte, said controller comprising said optical analyzer means using coherent light for continuously monitoring the concentration of said selected polymer in said out flowing solution, means for repeatedly adjusting a ratio of said inflows of said selected polymer and electrolyte, means responsive to said optical analyzer means for pre-storing a memory of an information curve for said selected polymer at each of said repeated adjustments, means for repeating said selection of polymers with a different polymer being selected on each repeated selection, said repeated adjustments being made for each of said different polymers until information curves have been stored in memory for all of said plurality of types of polymer, said information curve memories representing at least an output of said optical analyzer means vs said concentration for each of said plurality of types of polymer in said out flowing solution, means jointly responsive to said stored information curve memories derived from said repeated adjustments and to an output of said optical analyzer means for providing a usable process control signal for controlling said system, and means responsive to said process control signal for adjusting said inflows of polymer and electrolyte to maintain a selected concentration of any selected one type of polymer in said solution in order to process said selected one type of polymer.

2. The automatic controller means of claim 1 and means responsive to said usable process signal for displaying a readout in term of at least a percent of said one selected type of polymer concentration in said out flowing solution.

3. The automatic controller means of claim 1 wherein said polymer is a blend taken from a group consisting of emulsions, solutions, gels, and composites formed of said one selected type of polymer and water.

4. The automatic controller means of claim 1 wherein said polymer is a dispersion taken from a group consisting of emulsions, solutions, gels, and composites formed of at least polymer and water.

5. The automatic controller means of claim 1 wherein said polymer is activated and taken from a group consisting of emulsions, solutions, gels, and composites formed of at least polymer and water.

6. The automatic controller means of claim 1 wherein said polymer is a dairy product.

7. The automatic controller of claim 1 and power supply means, and means for delivering and for shutting down delivery of power from said power means to said analyzer means responsive to an occurrence of a destructive voltage spike.

8. The automatic controller of claim 1 wherein said optical analyzer means comprises a modular assembly housing containing therein a sample chamber for receiving said flowing solution, a laser diode for transmitting light through said flowing solution in said sample chamber, pick up means for detecting said transmitted light after having passed through said solution in said sample chamber, and a laser driver means for controlling said optical analyzer.

9. An automatic controller in combination with a polymer processing and delivery system for continuously controlling production of a polymer solution during operation of said polymer processing and delivery system, said controller comprising optical analyzer means using coherent light for continuously monitoring concentration of polymer solids and controlling a polymer solids/hydrocarbon concentration of a polymer solution product at least while the system is in operation, said analyzer means including a sample chamber coupled to continuously receive and at all times contain an instantaneous aqueous sample of said polymer solution product, means for emitting said coherent light with a controlled amplitude and frequency into said sample, said light energy being scattered and absorbed by the polymer material dispersed throughout the instantaneous aqueous sample within the sample chamber, optical receiver means for measuring an amount of said coherent light energy received after said light passes through said instantaneous sample, means for converting an output from said receiver means into a usable process control signal for controlling said polymer system in order to maintain a desired concentration and viscosity in said liquid, wherein said automatic controller comprising means for mixing any selected any one of a plurality of types of polymers and an electrolyte to produce an out flowing solution having a selected concentration of polymer in an electrolyte in a range of concentrations of said selected one type of polymer, means for transporting said solution through said sample chamber, means responsive to an effect which said solution produces on said light for giving an output signal representing instantaneous concentrations of said selected one type of polymer then being transported through said sample chamber, means for varying said concentration of said selected one type of polymer in incremental steps over said range, means responsive to said output signal prevailing after each of said incremental steps for storing a memory of the then inflow rates of said selected one type of polymer and electrolyte solution whereby at least one table of information relating said output signal to said selected one type of polymer concentration is stored in memory, means responsive to said stored table of information for automatically adjusting said processing system to maintain a selected concentration of said selected one type of polymer in said solution outflow, and means for selecting and repeating said incremental steps and storing of said table of information for each of said plurality of types of polymer.

10. The polymer controller of claim 9 and means for connecting said transporting means into said processing system for continuously monitoring said solution, a mode of making said connection being taken from a group consisting of by-pass, partial or full stream monitoring.

11. The polymer controller of claim 9 wherein said polymer processing system is a batch processing system and said means for connecting said transport means is coupled to measure said solution on a batch-by-batch basis.

12. The polymer controller of claim 9 wherein a separate table of said information is stored at an identifying address in said memory for each of said plurality of types of polymers that is processed by said controller, whereby a processing of each of said plurality of different types of polymers may be controlled in response to an interrogation of the memory for information stored at the address for that polymer.

13. The polymer controller of claim 9 wherein said light beam detecting means is a single modular housing containing therein a sample chamber through which said solution flows, means comprising a source of coherent light directed through said sample chamber to a photo pick up for receiving said coherent light exiting said chamber, and control means for driving said light beam detecting means.

14. An automatic controller in combination with a polymer processing and delivery system for continuously controlling production of a polymer solution during operation of said polymer processing and delivery system, said controller comprising optical analyzer means using coherent light for continuously monitoring a concentration of polymer solids and controlling a polymer solids/hydrocarbon concentration of a polymer solution product at least while the system is in operation, said analyzer means including a sample chamber coupled to continuously receive and at all times contain an instantaneous aqueous sample of said polymer solution product, means for emitting said coherent light with a controlled amplitude and frequency into said sample, said light energy being scattered and absorbed by the polymer material dispersed throughout the instantaneous aqueous sample within the sample chamber, optical receiver means for measuring an amount of said coherent light energy received after said light passes through said instantaneous sample, means for converting an output from said receiver means into a usable process control signal for controlling said polymer system in order to maintain a desired concentration and viscosity in said liquid, wherein said controller comprises means for measuring and giving an output signal indicating a concentration of each of a plurality of types of polymers in an out flowing solution of polymer and an electrolyte, means for incrementally adjusting in a plurality of steps the concentration for each of said plurality of types of polymers in said out flowing solution, means for storing a memory of said output signal and of said concentration for each of said plurality of types of polymers responsive to each incremental adjustment of said concentration in said out flowing solution, means jointly responsive to said output signal and said stored memory for maintaining a selected concentration of a selected one of said plurality of types of polymers in said out flowing solution, means for introducing polymer into said solution in varying amounts, means for introducing an electrolyte into said solution in varying amounts, and said means for maintaining said selected concentration of said selected one of said plurality of types of polymers adjusting the amounts of polymer and electrolyte introduced into said solution in response to a signal indicating a concentration of said out flowing solution and said stored memory.

15. The controller of claim 14 wherein said measuring means is a sample chamber through which said solution flows continuously, a source of light positioned to direct said light through the solution flowing through the sample chamber, detector means positioned to detect the light after it has passed through the solution, and means responsive to said detector means for giving said output signal.

16. A method of controlling a polymer processing and delivery system having an automatic controller for continuously controlling a production of a polymer solution during an operation of said polymer processing and delivery system, said controller comprising optical analyzer means using coherent light for continuously monitoring a concentration of polymer solids and for controlling a polymer solids/hydrocarbon concentration of a polymer solution product at least while the system is in operation, said analyzer including a sample chamber coupled to continuously receive and at all times contain an instantaneous aqueous sample of said polymer solution product, means for emitting said coherent light with a controlled amplitude and frequency into said sample, said light energy being scattered and absorbed by the polymer material dispersed throughout the instantaneous aqueous sample within the sample chamber, optical receiver means for measuring an amount of said coherent light energy received after said light passes through said instantaneous sample, means for converting an output from said receiver means into a usable process control signal for controlling said polymer system in order to maintain a desired concentration and viscosity in said liquid, said method comprising the steps of:

adjusting an incoming electrolyte flow rate to a minimum rate accommodated by said system, operating a source of neat polymer to successively deliver in incremental step a desired concentration for each of a plurality of types of polymers into said electrolyte, sensing the concentration of polymer in said electrolyte successive deliveries of said incremental steps of said concentrations, entering a reading of each of the sensed concentrations into a memory, repeating for each of said plurality of types of polymer the steps of said operation of said source of neat polymer at each of a plurality of concentrations of polymer, sensing the concentration and entering the reading, with each iteration of said repeated steps at different concentrations of said polymer in said electrolyte, separately storing data for each of said plurality of types of said polymers at separate addresses whereby any of said types of polymer can be processed in response to data stored at said address of that type of polymer, and operating said system to maintain any of said sensed concentrations in any selected one of said types of polymer in an outflow of electrolyte and polymer responsive to a selection of a particular reading stored at a selected address in a memory corresponding to the selected type of polymer.

17. The method of claim 16 and means for reducing rounding errors by reiterations of said reading in order to repeatedly reduce said rounding errors.

18. The method of claim 16 and the added step of calculating an offsetting scale responsive to said readings stored in said memory.

19. A computer controlled system for processing a selected one of a plurality of polymer and electrolyte combinations, said system comprising:

automatic controller means in combination with a polymer processing and delivery system for continuously controlling production of a polymer solution, said controller comprising optical analyzer means using coherent light for continuously monitoring a concentration of polymer solids and for controlling a polymer solids/hydrocarbon concentration of a polymer solution product at least while the system is in operation, said analyzer means including a sample chamber coupled to continuously receive and at all times contain an instantaneous aqueous sample of said polymer solution product, means for emitting said coherent light with a controlled amplitude and frequency into said sample, said light energy being scattered and absorbed by the polymer material dispersed throughout the instantaneous aqueous sample within the sample chamber, optical receiver means for measuring an amount of said coherent light energy received after said light passes through said instantaneous sample, means for converting an output from said receiver means into a usable process control signal for controlling said polymer system in order to maintain a desired concentration and viscosity in said liquid;

programmable means for sending and receiving data relative to flow rates of polymer and electrolyte while said polymer processing and system is processing any selected one of said plurality of polymer and electrolyte combinations, means comprising said optical analyzer means associated with an output of said system for monitoring a concentration of any selected one of said combinations of polymer and electrolyte during a processing of said selected one of said combinations, means for initializing said system by sending selected combinations of said plurality of polymers and electrolytes through said system with repeated step-by-step adjustments of said flow rates for each combination while storing data as a result of said repeated adjustments, said data collected by said monitoring means being stored in memory in said programmable means, and means for thereafter automatically processing any selected one of said polymer and electrolyte combinations in response to a selection of said stored data applicable to that combination and to a selected one of said repeated steps of that combination.

20. The computer controlled system of claim 19 and a variable speed neat polymer injection pump, and means jointly responsive to said computer and said stored data for changing the speed of said injection pump in response to an output of said monitoring means.

21. The computer controlled system of claim 19 wherein said monitor means comprises at least a source of laser light and means for selecting a frequency of said laser light in response to a type of polymer that is being monitored, means for passing said laser light through said selected combination of polymer and electrolyte, and means for picking up said light after it has passed through said combination and for giving a signal responsive to said picked up light.

22. A polymer processing system controller in combination with a polymer processing system comprising means for transporting a solution through a sample chamber, an optical analyzer means comprising means for directing a laser light beam through said solution while in said sample chamber whereby said solution has an effect upon said light, means for reading the light after said solution has had its effect upon the light, means responsive to said reading means for adjusting said polymer processing system to bring said light reading into a predetermined state, wherein said polymer processing system is a batch processing system and said means for connecting said transport means is coupled to measure said solution on a batch-by-batch basis, wherein said controller includes an automatic controller for controlling any selected one of a plurality of different types of polymers in an out flowing solution of said polymer processing system, said polymer processing system including means for feeding an adjusted inflow of a selected polymer in said batch into said polymer processing system, said selected polymer being one of said plurality of types of polymer, means for feeding an adjusted electrolyte inflow into said polymer processing system, means for delivering an outflow from said system comprising a solution having a combination of said selected polymer and electrolyte with a concentration of said selected polymer fixed by a relative proportion of said inflow of said selected polymer to said inflow of electrolyte, said automatic controller comprising said optical analyzer means for continuously monitoring the concentration of said selected polymer in said out flowing solution, means responsive to each of said plurality of different types of polymer for repeatedly adjusting a ratio of said inflows of said selected polymer and electrolyte, means responsive to said optical analyzer means for pre-storing a memory of an information curve for each of said selected polymer at each of said repeated adjustments, means for repeating said selection of polymers with a different polymer being selected on each repeated selection, said repeated adjustments being made for each of said different polymers until information curves have been stored in memory for all of said plurality of types of polymer, said information curve memories representing at least an output of said optical analyzer means vs said concentration for each of said plurality of types of polymer in said out flowing solution, means jointly responsive to said stored information curve memories derived from said repeated adjustments and to an output of said optical analyzer means for providing a usable process control signal for controlling said system, and means responsive to said process control signal for adjusting said inflows of polymer and electrolyte to maintain a selected concentration of any selected one type of polymer in said solution in order to process said selected one type of polymer.

* * * * *